US010653374B1

(12) United States Patent
Thomas et al.

(10) Patent No.: US 10,653,374 B1
(45) Date of Patent: May 19, 2020

(54) PORTABLE POSITRON EMISSION TOMOGRAPHY SCANNER HAVING A ROTATABLE DETECTOR RING WHICH CAN BE ROTATED 90 DEGREES FOR IMAGING A PATIENT IN A VERTICAL OR HORIZONTAL CONFIGURATION

(71) Applicants: Paul Bruce Thomas, San Pedro, CA (US); Farhad Daghighian, Santa Monica, CA (US)

(72) Inventors: Paul Bruce Thomas, San Pedro, CA (US); Farhad Daghighian, Santa Monica, CA (US)

(73) Assignee: Prescient Imaging, LLC, Hawthorne, CA (US)

(*) Notice: Subject to any disclaimer, the term of this patent is extended or adjusted under 35 U.S.C. 154(b) by 0 days.

(21) Appl. No.: 16/395,240

(22) Filed: Apr. 26, 2019

Related U.S. Application Data

(63) Continuation-in-part of application No. 15/420,069, filed on Jan. 30, 2017, now Pat. No. 10,307,120.

(51) Int. Cl.
A61B 6/00 (2006.01)
A61B 6/03 (2006.01)
A61B 5/055 (2006.01)

(52) U.S. Cl.
CPC ........... A61B 6/4405 (2013.01); A61B 6/037 (2013.01); A61B 6/4452 (2013.01); A61B 6/4476 (2013.01); A61B 5/0555 (2013.01); A61B 6/5235 (2013.01)

(58) Field of Classification Search
CPC ...... G01N 23/046; A61B 6/4405; A61B 6/037
See application file for complete search history.

(56) References Cited

U.S. PATENT DOCUMENTS

| 4,316,091 | A | 2/1982 | Bernardi |
| 5,042,478 | A | 8/1991 | Marquardt |
| 8,055,325 | B1 | 11/2011 | Damadian et al. |
| 9,700,272 | B2* | 7/2017 | Gregerson ........... A61B 5/0555 |
| 2005/0138731 | A1 | 6/2005 | Failor et al. |
| 2008/0081992 | A1* | 4/2008 | Kagermeier ......... A61B 6/4405 600/425 |
| 2011/0222667 | A1* | 9/2011 | Gregerson ............ A61B 6/035 378/198 |
| 2011/0306864 | A1* | 12/2011 | Zarate .................. A61B 6/4405 600/407 |
| 2013/0028390 | A1* | 1/2013 | Kalenyak ............... A61B 6/035 378/197 |

(Continued)

Primary Examiner — Yara B Green
(74) Attorney, Agent, or Firm — Jerry Fong

(57) ABSTRACT

A portable positron emission tomography (PET) scanner includes a rotatable scan detector ring which can be rotated 90 degrees for imaging a patient in a vertical or horizontal orientation. In the vertical orientation, a patient can be standing or seating such that the aperture of the scan detector ring is raised to allow the patient to be within the scanning region and lower to perform the image scanning on the patient. In the horizontal orientation, a patient must be lying down on a platform whereby the platform is moved within the aperture of the scan detector ring to perform the image scanning on the patient. In this horizontal orientation, the scan detector ring is also stowed and secured to be moved to other scanning locations.

13 Claims, 15 Drawing Sheets

(56) References Cited

U.S. PATENT DOCUMENTS

| | | | |
|---|---|---|---|
| 2014/0098930 A1* | 4/2014 | Litzenberger | A61B 6/548 378/4 |
| 2015/0208992 A1 | 7/2015 | Marash et al. | |
| 2016/0128653 A1* | 5/2016 | Fortuna | A61B 6/035 378/12 |
| 2016/0338656 A1* | 11/2016 | Gregerson | A61B 5/0555 |
| 2017/0071560 A1* | 3/2017 | Gregerson | A61B 6/4447 |
| 2018/0289339 A1* | 10/2018 | Fortuna | A61B 6/0407 |

* cited by examiner

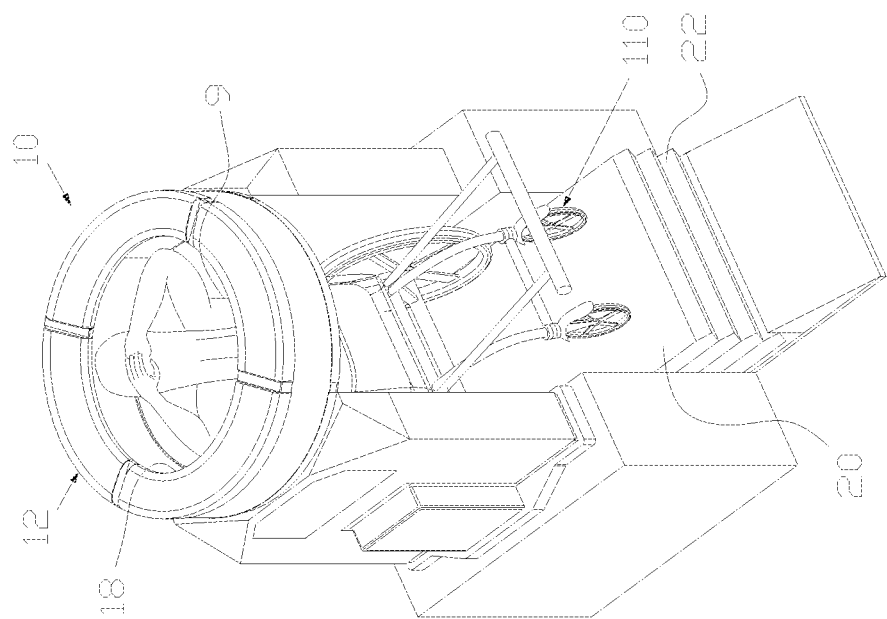
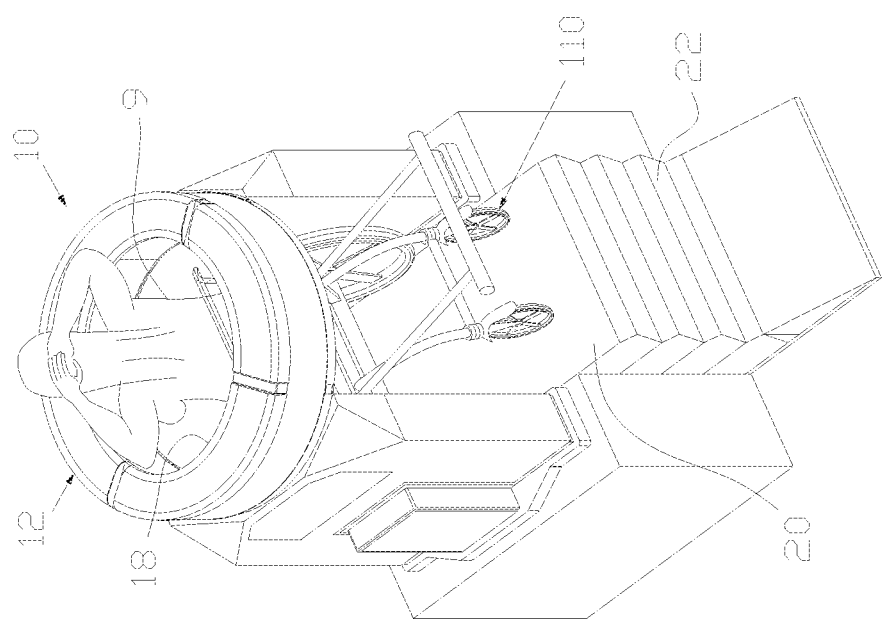

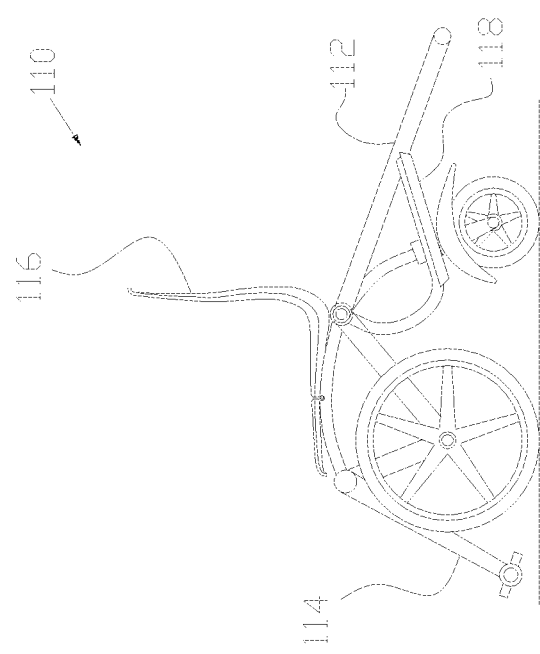

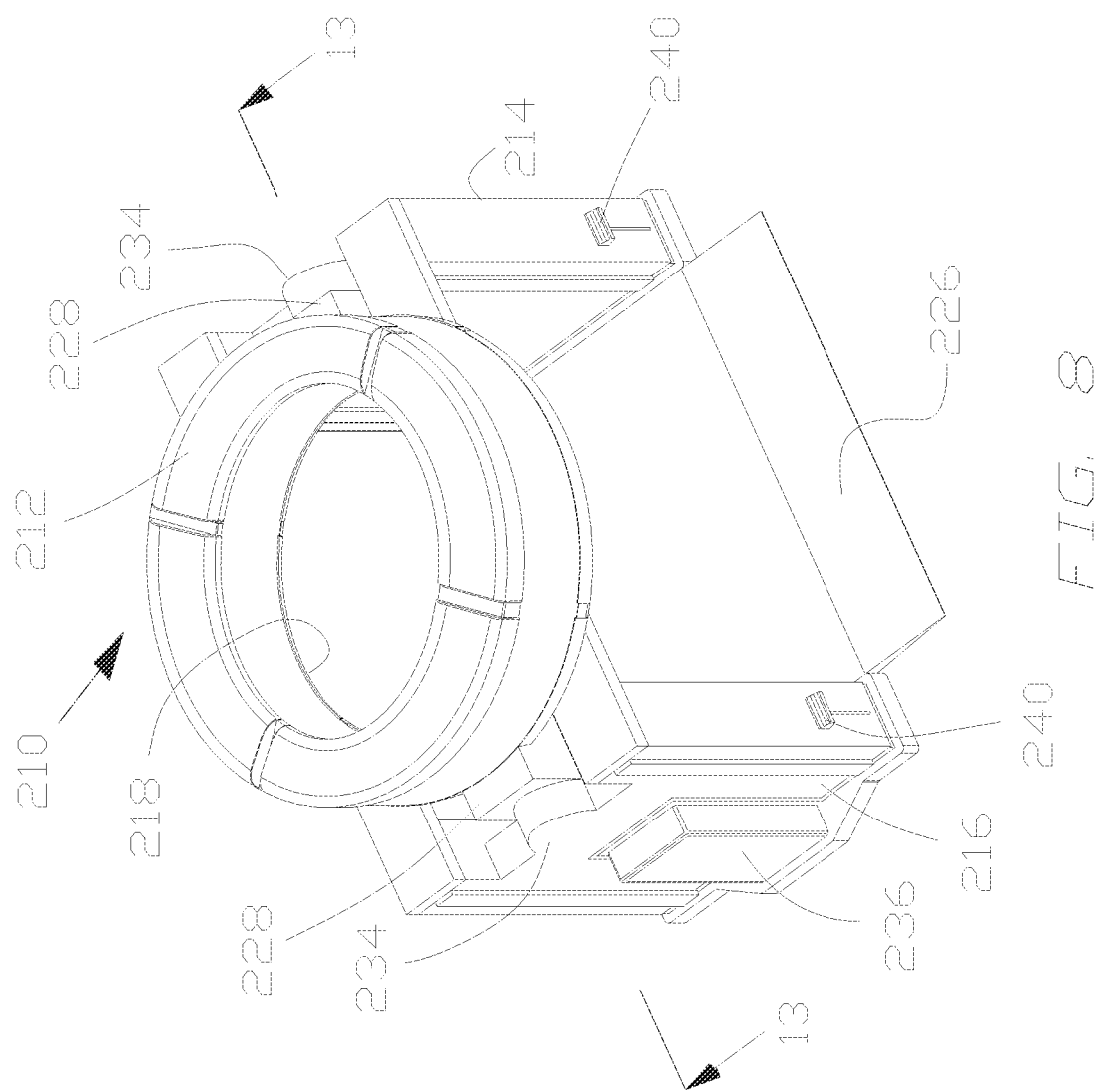

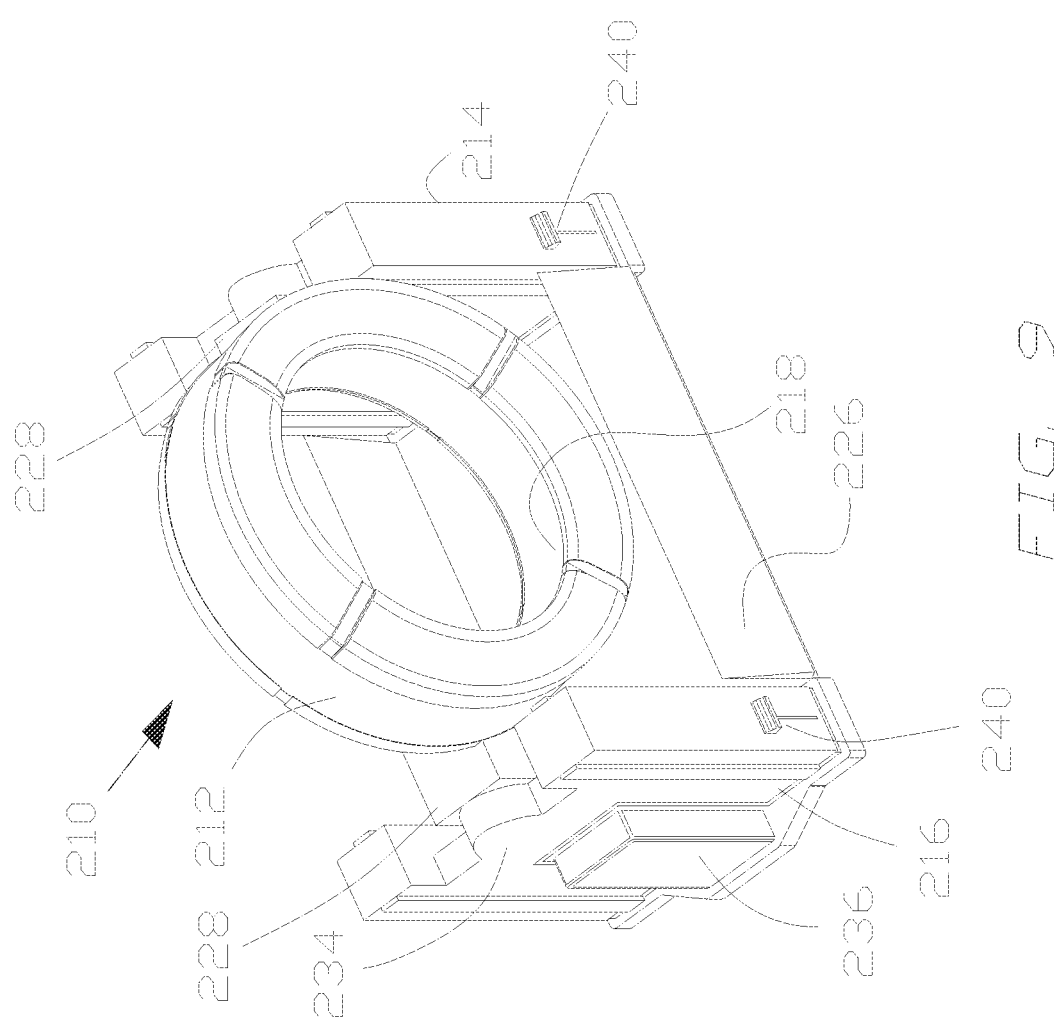

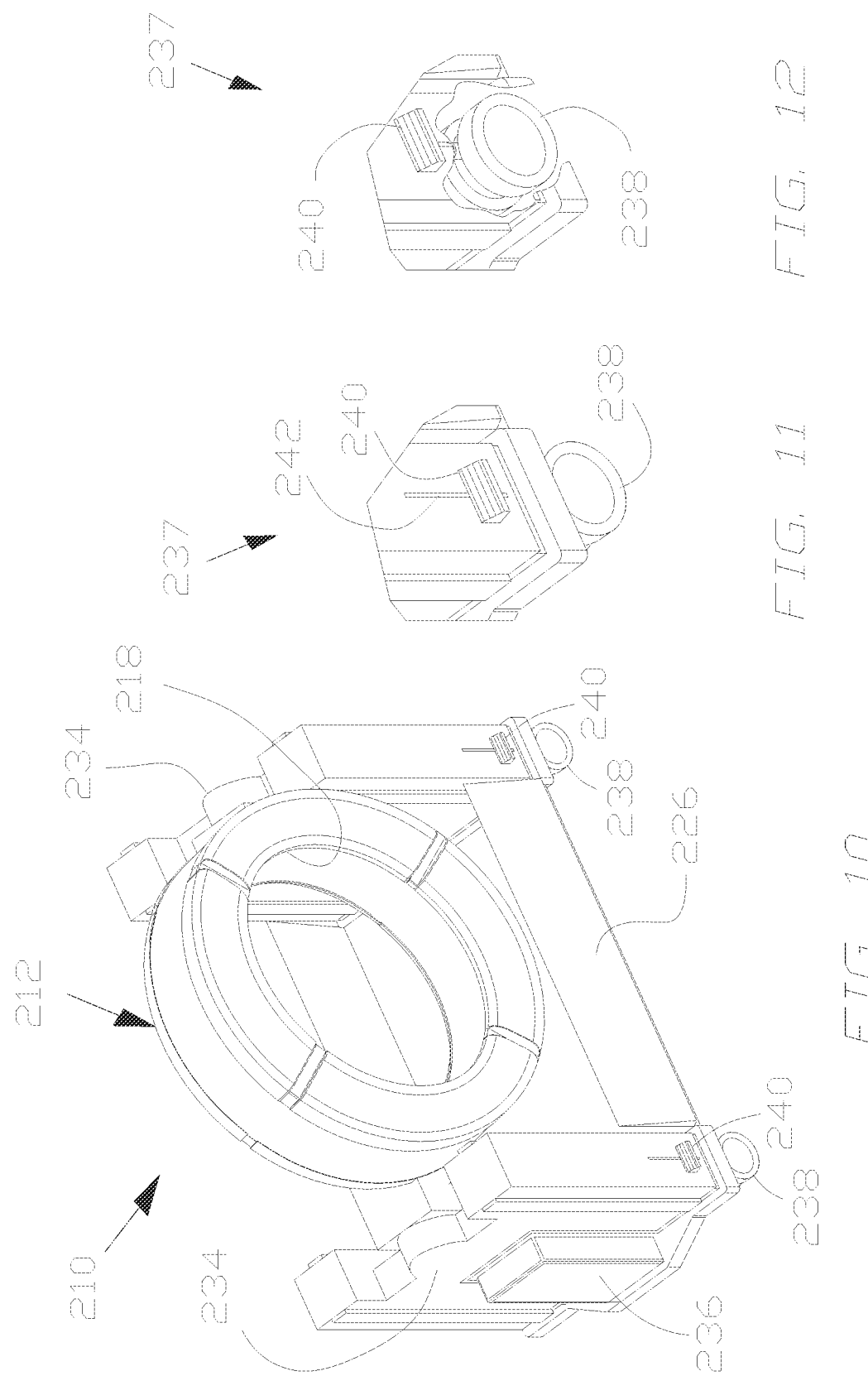

PORTABLE POSITRON EMISSION TOMOGRAPHY SCANNER HAVING A ROTATABLE DETECTOR RING WHICH CAN BE ROTATED 90 DEGREES FOR IMAGING A PATIENT IN A VERTICAL OR HORIZONTAL CONFIGURATION

BACKGROUND OF THE INVENTION

1. Field of the Invention

The present invention generally relates to medical imaging systems. More particularly, the present invention relates to a vertical-moving horizontal ring PET scanner. In particular, the present invention relates to a portable positron emission tomography (PET) scanner having a detector ring rotatable 90 degrees for imaging a patient in a vertical or horizontal configuration.

2. Description of the Prior Art

Medical imaging technology has made remarkable advances over the years including developments and improvements on positron emission tomography (PET). The use of PET has grown in the field of medical imaging. PET has gained attention as being effective in making an early diagnosis of cancers, heart diseases, cerebrovascular disorders, dementia and others. PET is an imaging method that relies on injecting IV, a compound labeled with a trace amount of a positron emitting nuclide. The PET's detector ring identifies paired photons (511 keV of energy each) produced by the positron annihilation effect. The paired 511 keV photons travel in the opposite direction at a 180° angle from each other. Therefore, positron decay can be localized without collimation, as used for SPECT, but with the use of the principle of coincidence detection. As PET cameras do not necessitate collimators, these systems have a much higher sensitivity than do SPECT cameras. PET scan is a map of radioactive concentration in various tissues based on the specific biochemical properties of the tracer. For example, metabolism of glucose or blood flow in heart muscle (myocardium), and examining the presence or absence of a disease and the seriousness of a disease, and prognoses during the course of therapy. For the implementation thereof, PET scanners have been put into practical use. Another advantage of PET vs. SPECT is its capability to measure the radioactive concentration inside the body without the disturbing effect of tissue attenuation.

PET-myocardial perfusion imaging (MPI) allows accurate measurement of myocardial perfusion, absolute myocardial blood flow and function at stress and rest in a single study session performed in approximately 30 minutes. Various PET tracers are available for MPI and rubidium-82 or nitrogen-13-ammonia is most commonly used. Relative quantification of PET perfusion images shows very high diagnostic accuracy for detection of obstructive coronary artery disease. Dynamic myocardial blood flow analysis has demonstrated additional prognostic value beyond relative perfusion imaging.

A PET Myocardial Perfusion Imaging (MPI) Stress Test consists of intravenous injection of Ru-82 or N-13 labeled ammonia while the heart is at rest. These isotopes have relatively short half-lives (76 seconds and 9.8 minutes respectively). After a few minutes of imaging the heart at rest, the patient is asked to exercise on a treadmill or a stationary cycle. When the heart reaches its peak stress, a second IV injection of the radioactive tracer and a second set of "stress" images are collected by the PET scanner. If a region of the myocardium shows relative lower uptake of radioactivity in the resting image, it may indicate infarct in the myocardium. If the resting image is uniform, but a defect is shown in the "stress" image, it is a sign of ischemia in that region.

Ischemic heart disease (IHD) remains a major healthcare issue in the United States, and often results in myocardial infarction (MI) and adverse post-MI left ventricle (LV) remodeling, which manifests as changes in LV structure, volume, geometry, and function. An estimated eight million people are afflicted with MI in the United States with around 610,000 new cases reported each year.

Significant progress has been made in the development of dynamic positron emission tomography (PET) perfusion imaging to accurately quantify coronary flow reserve, CFR as the ratio of absolute global myocardial blood flow (MBF) measured at peak stress (i.e. during vasodilator induced hyperemia) over that at rest (which is corrected for rate-pressure product as an index of baseline cardiac work). From a pathophysiologic perspective, CFR provides a measure of the integrated effects of epicardial coronary artery disease CAD, diffuse atherosclerosis, vessel remodeling, and microvascular dysfunction on myocardial tissue perfusion.

In contrast to SPECT, PET offers the possibility to routinely quantify perfusion in absolute terms and calculate coronary flow reserve (CFR), which has incremental prognostic value over evaluation of perfusion defects alone. It is demonstrated that a blunted CFR was one of the strongest prognostic factors and trumps clinical risk scores as well as relative perfusion abnormalities.

Conventionally, a cylindrical geometry is the design of choice for a PET scanner. As shown in FIG. 1, the cylindrical geometry can capture all events in the transaxial plane. The axial extent of the detector will determine how many such planes can be defined, as well as how many oblique planes can be utilized.

The following five (5) patents and published patent applications are the closest prior art references to the present invention.

1. U.S. Pat. No. 4,316,091 issued to Bernardi on Feb. 16, 1982 for "CT Scanner" (hereafter the "Bernardi");

2. U.S. Pat. No. 5,042,487 issued to Marquardt on Aug. 27, 1991 for "Examination Unit Including Positionable Patient Chair, Examination Device And Support System" (hereafter the "Marquardt");

3. U.S. Pat. No. 8,055,325 issued to Damadian et al. on Nov. 8, 2011 for "Seated Patient Support And Use Thereof In Magnetic Resonance Imaging" (hereafter the "Damadian");

4. Patent Application Publication No. 2005/0138731 issued to Failor et al. on Jun. 30, 2005 for "Multi-Purpose Patient Chair" (hereafter the "Failor"); and 5. Patent Application Publication No. 2015/0208992 issued to Marash et al. on Jul. 30, 2015 for "Apparatus And Method For Providing Patient Imaging" (hereafter the "Marash").

The Bernardi discloses a computed tomography (CT) scanner which includes a pair of uprights secured to a base unit. A yoke surrounds the uprights and a pair of side arms for holding a ring housing. The yoke and the pair of side arms support the ring housing which would require massive supports to function accurately with stability and providing this type of support mechanism would not provide an accurate image of the organ areas of the patient.

The Marquardt discloses an apparatus and method for medically examining a patient's spine using a non-invasive technique such as a computed tomography (CT).

The Damadian discloses a seated patient support and use thereof in magnetic resonance imaging.

The Failor discloses a multi-purpose patient chair which provides a radiolucent backrest pivotally secured to a seat section.

The Marash discloses a patient support platform which includes a support arm, an extension arm, a rotation member, and a rotation ring.

SUMMARY OF THE INVENTION

A PET scanner is a large scanning machine with a usually round, doughnut shaped hole in the middle, similar to a computed tomography (CT) or magnetic resonance imaging (MRI) unit. Within this PET scanner are multiple detectors that record the annihilation photons emitted from the radiotracer in a patient's body. The present invention relates to an independent vertical-moving horizontal PET detector ring thereby enabling scanning a patient in seated or standing position, and consequently decreasing the footprint of the whole system. This seating position has distinct advantages, particularly in scanning the heart that will be described below.

In order to measure the value of coronary flow reserve (CFR), the PET imaging should start immediately after the heart reaches its peak stress level. This is not possible if treadmill is used to stress the patient because it takes time for the patient to walk to the PET scanner and be positioned for imaging.

With the present invention of a vertical PET scanner and a stationary cycle for "stressing" the patient while positioned inside the PET detector ring, scanning can start immediately after the heart reaches its peak stress. This allows quantification of myocardial blood flow, as well as the myocardial flow reserve that is important for diagnosis of microvascular disease, a very important issue especially for women.

The present invention relates to a portable PET scanner having a rotatable scan detector ring which can be rotated 90 degrees for imaging a patient in a vertical or horizontal configuration. In the vertical configuration, a patient can be standing or seating such that the aperture of the scan detector ring is raised to allow the patient to be within the scanning area and lower to perform the image scanning on the patient. In the vertical configuration, the aperture of the scan detector ring is parallel to the ground.

In the horizontal configuration, a patient must be lying down on a platform whereby the platform is moved within the aperture of the scan detector ring to perform the image scanning on the patient. In the horizontal configuration, the aperture of the scan detector ring is parallel to a wall of a room. Also in the horizontal configuration, the scan detector ring of the PET scanner is stored and secured to be moved to other scanning locations.

The alternative embodiment of the present invention portable PET scanner is used with a transport apparatus for transporting the portable PET scanner to other locations for scanning. In this embodiment, the transport apparatus is detachable from the PET scanner to be used in conjunction with a gantry patient platform for imaging a patient in the horizontal configuration.

Further novel features and other objects of the present invention will become apparent from the following detailed description, discussion and the appended claims, taken in conjunction with the drawings.

BRIEF DESCRIPTION OF THE DRAWINGS

Referring particularly to the drawings for the purpose of illustration only and not limitation, there is illustrated:

FIGS. 5a and 5b illustrate an alternative embodiment of the present invention PET scanner with a horizontal aperture detector ring situated on a platform, where a patient is sitting in a wheelchair and rolled into a vertical lift to be raised or lowered into position for scanning;

FIG. 7c illustrates the specialized wheelchair shown in FIG. 7a in a scanning position to be used in conjunction with the present invention vertical-moving PET scanner shown in FIG. 2;

FIG. 8 is a perspective view of the present invention portable PET scanner for imaging a patient in a vertical orientation;

FIG. 9 is a perspective view of the present invention portable PET scanner for imaging a patient in a horizontal orientation, where the scan detector ring is also in the stowed position;

FIG. 10 is a perspective view of the present invention portable PET scanner showing a rotatable scan detector ring stowed and the wheel mechanisms deployed;

FIG. 11 is an enlarged exploded perspective view of the wheel mechanism in a deployed position;

FIG. 12 is an enlarged exploded perspective view of the wheel mechanism in a retracted or stowed position;

DETAILED DESCRIPTION OF THE EMBODIMENTS OF THE PRESENT INVENTION

Although specific embodiments of the present invention will now be described with reference to the drawings, it should be understood that such embodiments are by way of example only and merely illustrative of but a small number of the many possible specific embodiments which can represent applications of the principles of the present invention. Various changes and modifications obvious to one skilled in the art to which the present invention pertains are deemed to be within the spirit, scope and contemplation of the present invention as further defined in the appended claims.

Described briefly, the present invention relates to a vertically-moving horizontal aperture body scanner, so that it's 360° detector ring can be positioned and re-positioned. At the highest position of the detector ring provides an unobstructed path for patient insertion and removal. The detector ring has multiple downward positions which permit sections of 360° scans with multiple slices. Scans could also be sequenced from the bottom position upwards. Vertically seated or standing patients can benefit from analysis of heart and other scanned areas of the body subjected to stress by exercise during, or immediately before scans. The mass of the detector ring and its sensitive sensors and electronics is secured for stable vertical movement by distributed lift mechanisms. There is the added option wherein a patient could be scanned, a procedure performed such as a biopsy, and then scanned to verify the procedure. Other modalities of medical imaging can be performed and the resulting imaging fused to the PET images. Vertical positioning scanning is more compact for a seated or standing patient. Scanning time savings is accomplished by using a specialized wheelchair, because positioning of the patient is done outside the PET scanner and even the initial part of the exercising can happen while another patient is being scanned. By having multiple specialized wheelchairs available, a higher throughput can be achieved in a medical imaging center.

Figure 1:
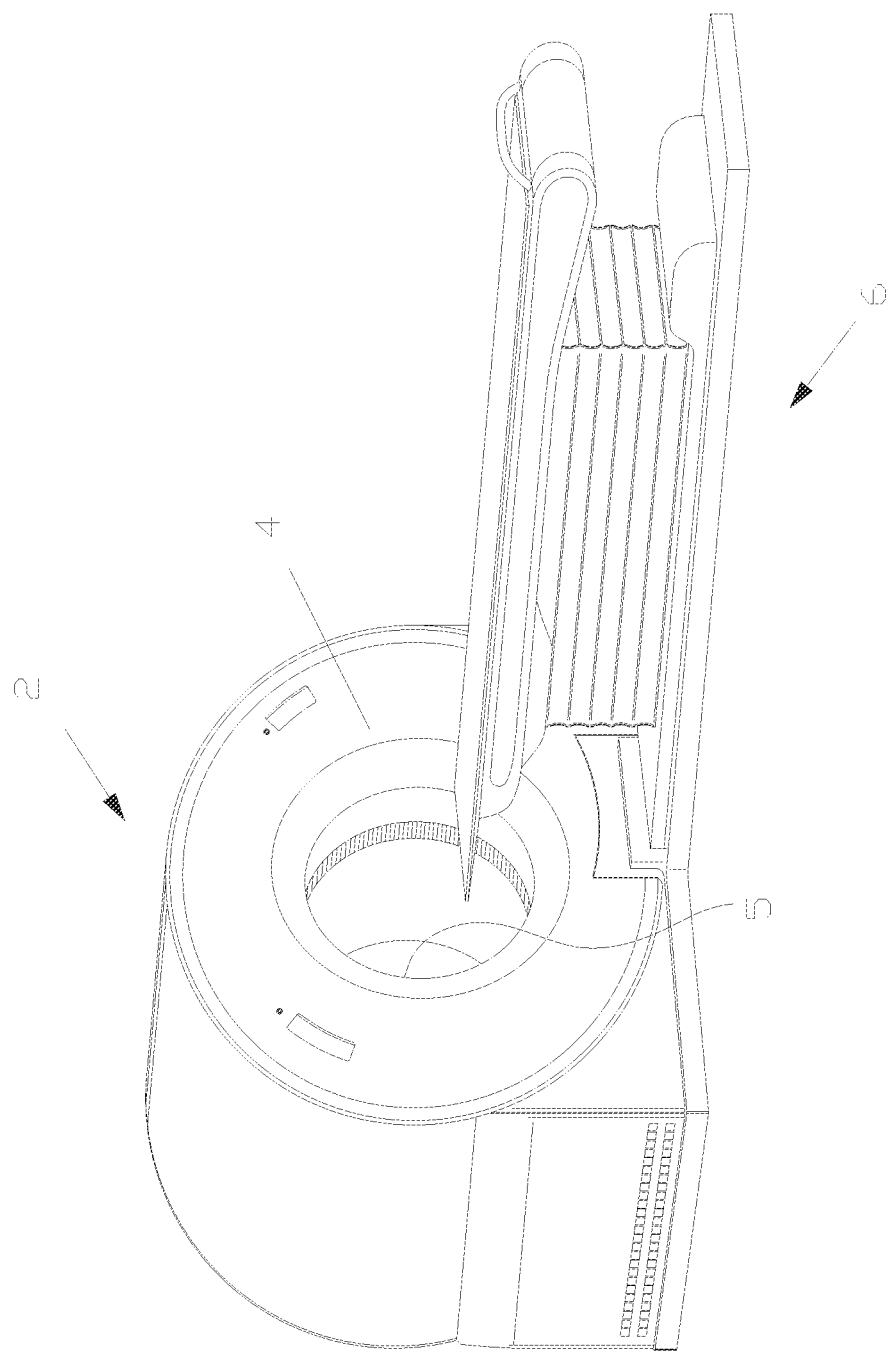
FIG. 1 is a perspective view of a prior art positron emission tomography (PET) scanner with a gantry table.

Referring to FIG. 1, there is shown a prior art positron emission tomography (PET) scanner 2 which comprises a vertical ring detector 4, a gantry table 6, and a computer system (not shown). A support on the gantry table 6 is horizontally moved into the bore 5 of the detector ring 4 in response to commands received from the computer system. The computer system typically includes a display and one or more input devices such as a keyboard or a mouse. Through the keyboard and associated input devices, the operator can control the operation of the PET scanner 2 and the display of the resulting images on the display.

Figure 2:
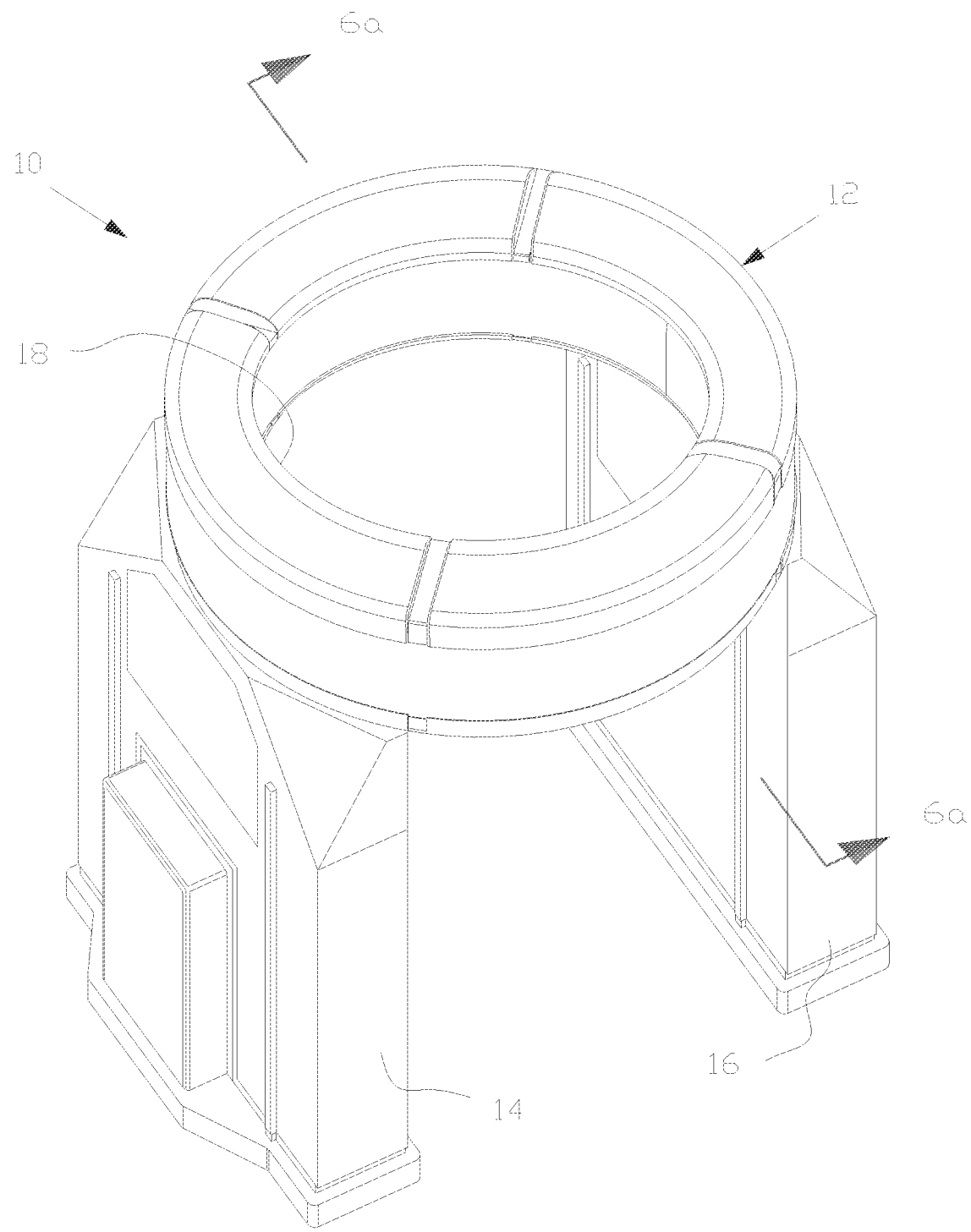
FIG. 2 is a perspective view of the present invention vertical-moving PET scanner with a horizontal aperture detector ring.

Referring to FIG. 2, there is shown the present invention vertical-moving PET scanner 10 which includes a horizontal aperture scan detector ring 12 and two opposite support lifting structures 14 and 16. The scan detector ring 12 has a horizontal aperture 18 which is configured and situated substantially parallel to the floor. The PET scanner 10 is well known and conventional in the art, and the description will not be described in details but will only be described in general terms as the PET scanner 10. The mass of the scan detector ring 12 and its sensitive sensors and electronics is secured for stable vertical movement by distributed support lifting structures 14 and 16.

Figure 3C:
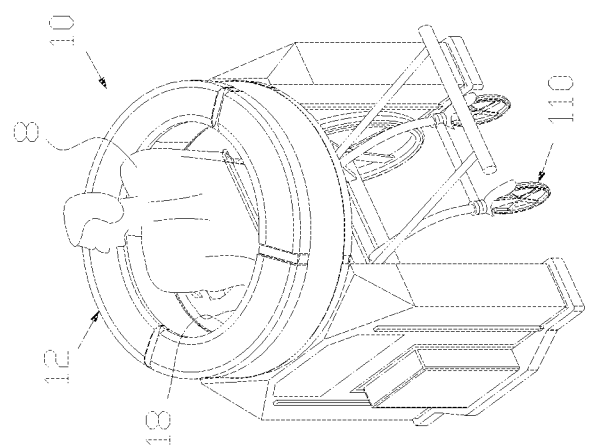
FIG. 3c illustrates the present invention vertical-moving PET scanner with the horizontal aperture detector ring in a lower cardiac scanning position while the patient is in the wheelchair.
Figure 3B:
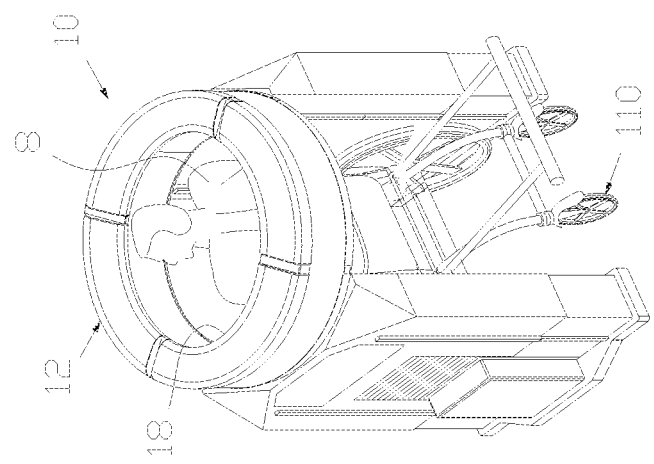
FIG. 3b illustrates the present invention vertical-moving PET scanner with the horizontal aperture detector ring being lowered into position for imaging while the patient is sitting in the wheelchair.
Figure 3A:
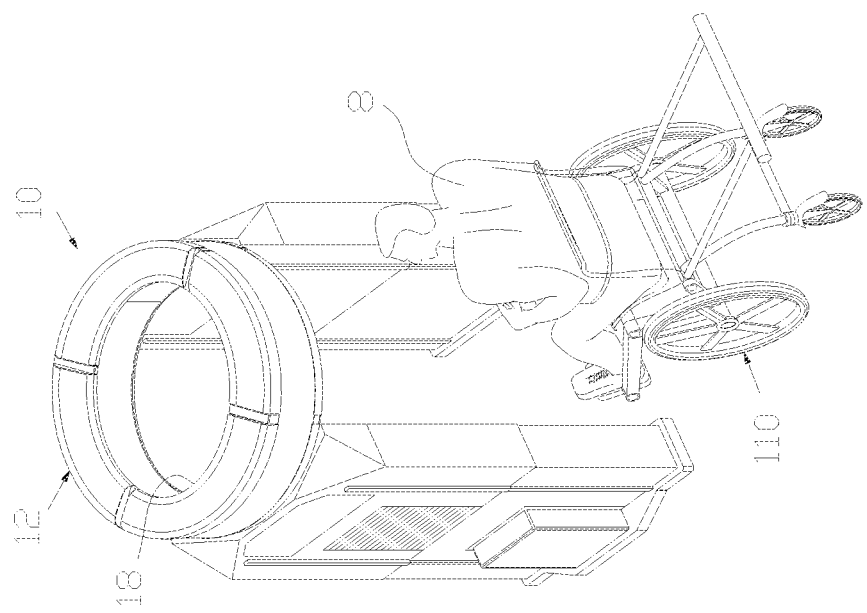
FIG. 3a illustrates the present invention vertical-moving PET scanner with the horizontal aperture detector ring at its highest vertical position for a patient in a wheelchair to be rolled into position for scanning.

Referring to FIG. 3a, there is shown the vertical-moving PET scanner 10 with the horizontal aperture 18 of the detector ring 12 at its highest vertical position for a patient 8 sitting in a specialized wheelchair 110 to be rolled into position for image scanning.

Referring to FIG. 3b, there is shown the vertical-moving PET scanner 10 with the horizontal aperture 18 of the detector ring 12 being lower while the patient 8 is sitting in the wheelchair 110 to be scanned.

Referring to FIG. 3c, there is shown the vertical-moving PET scanner 10 with the horizontal aperture 18 of the detector ring 12 in a lower cardiac scan position while the patient 8 is sitting in the wheelchair 110 to be scanned.

Figure 4B:
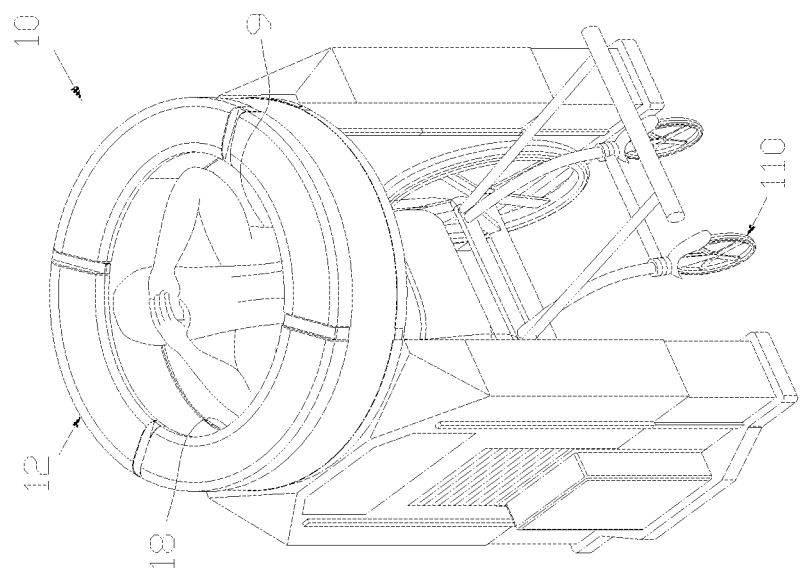
FIG. 4b illustrates the present invention vertical-moving PET scanner with the horizontal aperture detector ring in a raised position to allow a doctor to perform a biopsy on the patient, or other types of imaging (e.g. ultrasound or x-ray mammogram) while sitting in the wheelchair.
Figure 4A:
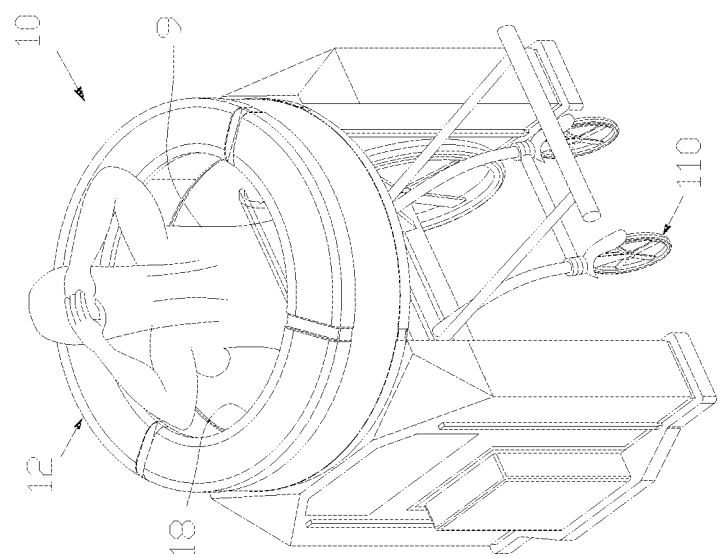
FIG. 4a illustrates the present invention vertical-moving PET scanner with the horizontal aperture detector ring in a lower chest scanning position to scan the breast area of the patient sitting in the wheelchair.

Referring to FIG. 4a, there is shown the vertical-moving PET scanner 10 with the horizontal aperture 18 of the detector ring 12 in a lower chest scanning position to scan the breast area of the patient 9 sitting in the wheelchair 110.

Referring to FIG. 4b, there is shown the vertical-moving PET scanner 10 with the horizontal aperture 18 of the detector ring 12 in a raised position to allow a doctor to perform a biopsy, deliver local therapy guided by the PET image, or other imaging procedures on the patient 9 sitting in the wheelchair 110.

Referring to FIG. 5a, there is shown an alternative embodiment of the vertical-moving PET scanner 10 situated on a platform 20, where a patient 9 is sitting in a wheelchair 110 and rolled into a middle vertical lift 22 and raised into position for PET scanning.

Referring to FIG. 5b, there is shown the alternative embodiment of the vertical-moving PET scanner 10 situated on the platform 20, where the patient 9 is sitting in the wheelchair 110 and rolled into the middle vertical lift 22 for PET scanning.

Figure 6B:
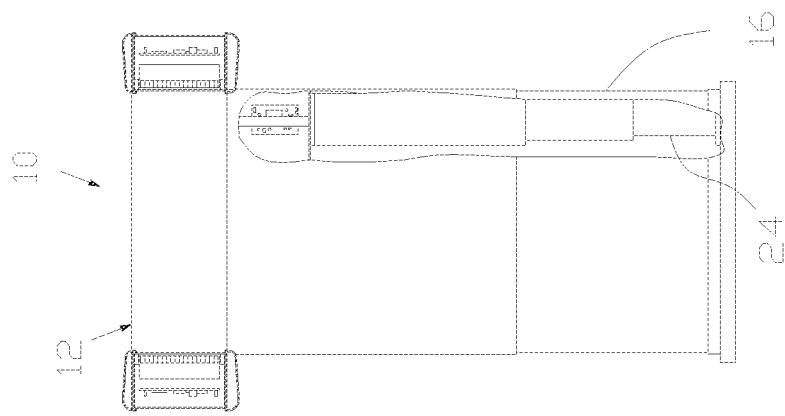
FIG. 6b is a cross sectional view of the present invention vertical-moving PET scanner with the horizontal aperture detector ring at its highest vertical position, showing the basic construction elements.
Figure 6A:
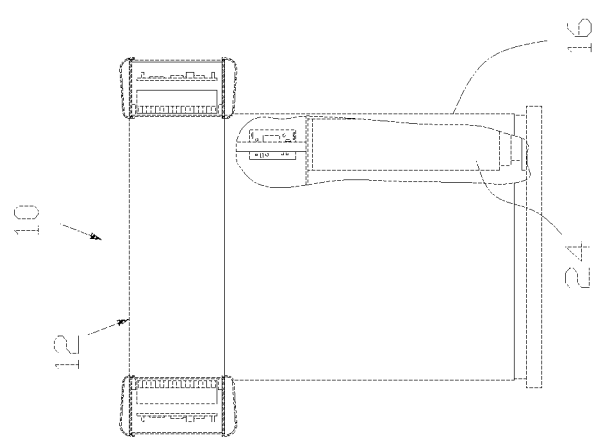
FIG. 6a is a cross sectional view of the present invention vertical-moving PET scanner with the horizontal aperture scan ring at its lowest position, showing the basic construction elements and taken along lines 6a-6a of FIG. 2.

Referring to FIG. 6a, there is shown a cross sectional view taken along lines 6a-6a of the present invention vertical-moving PET scanner 10 with the horizontal aperture 18 of the detector ring 12 at its lowest position, showing the basic construction elements.

Referring to FIG. 6b, there is shown a cross sectional view of the present invention vertical-moving PET scanner 10 with the horizontal aperture scan ring 12 at its highest vertical position, showing the basic construction elements. Each of the support lifting structures 14 and 16 includes two opposite lifting columns 24 which are identical. Each lifting column 24 can be raised or lowered by electrical motor or hydraulic system known in the art. These four lifting columns 24 are utilized to distribute the weight of the horizontal aperture detector ring 12 to be raised or lowered by the computer system.

Figure 7B:
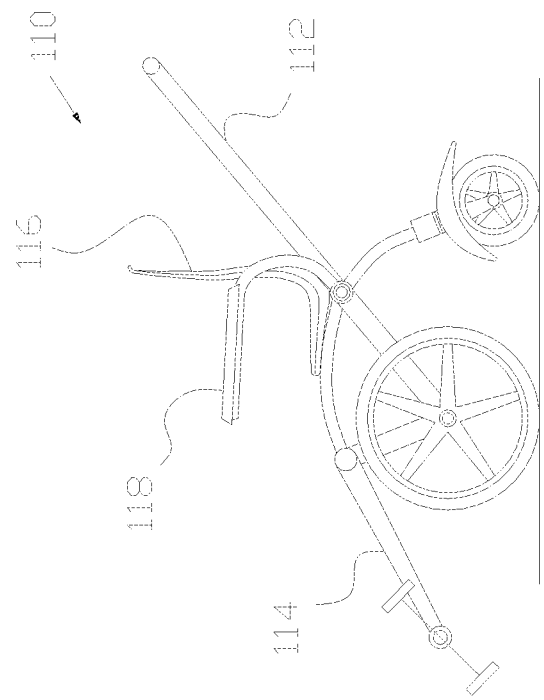
FIG. 7b illustrates the specialized wheelchair shown in FIG. 7a in an exercise position to be used in conjunction with the present invention vertical-moving PET scanner with a horizontal aperture scan ring shown in FIG. 2.
Figure 7A:
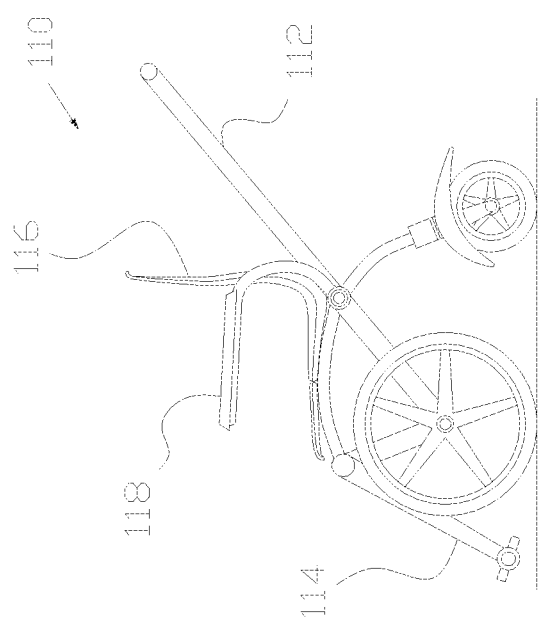
FIG. 7a illustrates a specialized wheelchair for cardiac imaging in a transport position to be used in conjunction with the present invention vertical-moving PET scanner with a horizontal aperture scan ring shown in FIG. 2.

Referring to FIG. 7a, there is shown a specialized wheelchair 110 in a transport position to be used in conjunction with the present invention vertical-moving PET scanner 10 with a horizontal aperture detector ring 12 shown in FIG. 2.

The wheelchair 110 includes a pivot handlebar portion 112, a seat portion 116, a leg portion 114, and an arm portion 118. The handlebar portion 112 and the leg portion 114 are shown in its transport position.

Referring to FIG. 7b, there is shown the specialized wheelchair 110 in its exercise position to be used in conjunction with the present invention vertical-moving PET scanner 10 shown in FIG. 2.

In the exercise position, the leg portion 114 is extended as shown to allow the patient sitting in the wheelchair 110 to exercise.

Referring to FIG. 7c, there is shown the specialized wheelchair 110 in its scanning position to be used in conjunction with the present invention vertical-moving PET scanner 10 shown in FIG. 2.

In the scanning position, the leg portion 114 is positioned downwardly and both the handlebar portion 112 and the arm portion 118 are pivoted down to allow the patient sitting in the seat portion 116 to be scanned together without any issue.

The configuration or placement of the horizontal aperture detector ring 18 can be utilized with other imaging devices, such a computed tomography (CT) unit or a magnetic resonance imaging (MRI) unit or etc.

The present invention can also be a method of scanning a patient's body vertically seated or standing and can benefit from analysis of heart and other scanned areas of the body subjected to stress by exercise during, or immediately before scans.

Figure 14:
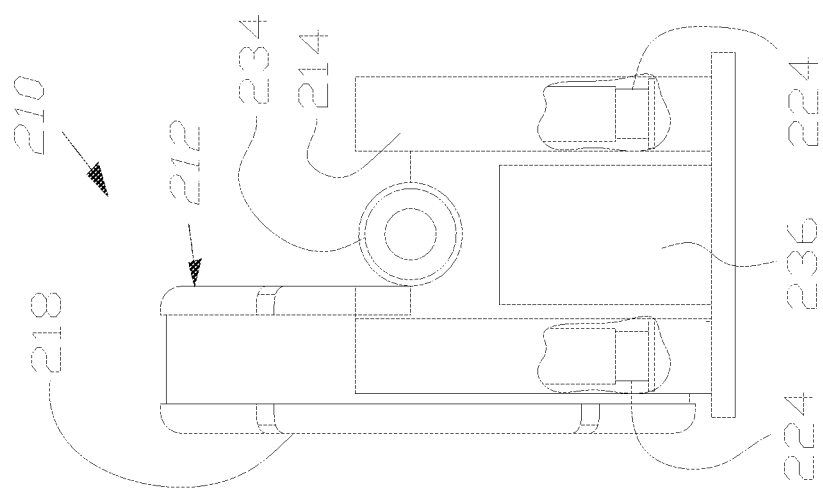
FIG. 14 is a side elevational view of the present invention portable PET scanner.
Figure 13:
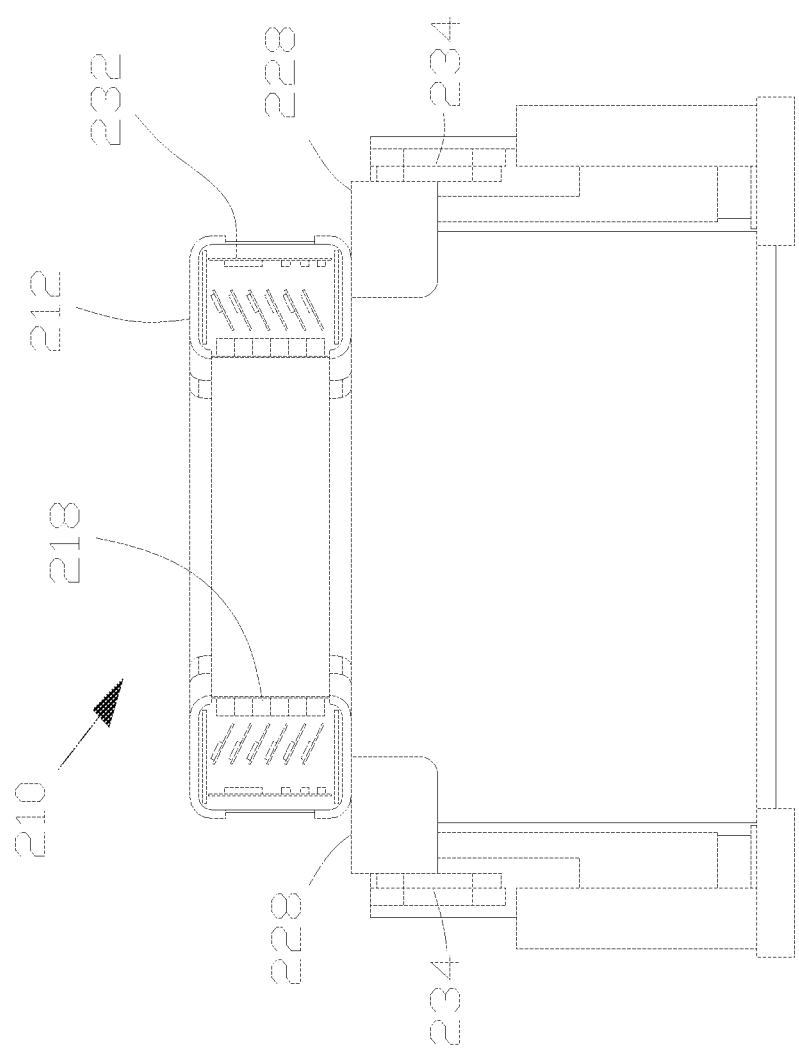
FIG. 13 is a cross sectional view of the present invention portable PET scanner taken along lines 13-13 of FIG. 8 and showing the basic construction elements.

Referring to FIGS. 8, 13, and 14, there is shown the present invention portable positron emission tomography (PET) scanner 210 which comprises a scan detector ring 212 and a computer system (not shown) for controlling the imaging of the PET scanner 210. The present invention PET scanner 210 can also be used with a gantry table 206 (shown in FIG. 15). In response to commands received from the computer system, the scan detector ring 212 of the portable PET scanner 210 is moved to image a patient in the scanning area of the scan detector ring 212. The computer system typically includes a monitor and one or more input devices such as a keyboard or a mouse. Through the keyboard and associated input devices, the operator can control the operation of the PET scanner 210 and the display of the resulting images on the computer monitor.

Referring to FIGS. 13 and 14, the portable PET scanner 210 is well known and conventional in the art, and the description will not be described in details but will only be described in general terms as the PET scanner 210. The mass of the scan detector ring 212 and its sensitive sensors and electronics 232 are secured within the detector ring 212 for stable vertical movement by the distributed right and left support lifting structures 214 and 216. Each of the support lifting structures 214 and 216 includes two opposite lifting columns 224 which are identical. Each lifting column 224 can be raised or lowered by electrical motor or hydraulic system known in the art. These four lifting columns 224 are synchronized and utilized to distribute the weight of the detector ring 212 to be raised or lowered by the computer system.

Referring to FIGS. 8, 9, 10, 13, and 14, the scan detector ring 212 includes a circular shaped aperture 218. For example, the detector ring 212 can be non-circular. The scan detector ring 212 has a detector depth of at least four inches and an inner diameter of at least nine inches for fully imaging a cross section of significant organ areas of a patient. Alternatively, the scan detector ring 212 has a detector depth of at least four inches to six inches and an inner diameter of at least nine inches to sixty inches.

The portable PET scanner 210 includes a ramp 226 for allowing a patient to be situated in the scanning area of the scan detector ring 212. Two opposite mounting support brackets 228 are attached to the scan detector ring 212 at opposite sides to provide support to the scan detector ring 212. The mounting support brackets 228 maintain the scan detector ring 212 on top of the support lifting structures 214 and 216. Two rotating slew rings 234 are respectively mounted within the two opposite mounting support brackets 228. The rotating slew ring 234 is a rotational rolling element bearing that typically supports a ring mechanism for slow-turning or slow-oscillating load. The rotating slew ring 234 is used for self-lubricating, low-friction sliding elements in place of ball bearings.

The scan detector ring 212 can be manually rotated by the slew rings 234 for rotating 90 degrees to unlock and lock in the vertical configuration (see FIG. 9) or horizontal configuration (see FIG. 8) for imaging a patient in both the vertical and horizontal configurations. In the horizontal orientation, the aperture 218 of the scan detector ring 212 is parallel to the floor (see FIG. 8). In the vertical orientation, the aperture 218 of the scan detector ring 212 is parallel to a wall of a room (see FIG. 9). It is possible that the scan detector ring 212 can be rotated to image the patient in various orientations.

Referring to FIGS. 10, 11 and 12, there are shown wheel assemblies 237 located underneath the lifting structure 214 and 216 for moving the PET scanner 210 to different locations for imaging. Each wheel assembly 237 includes a wheel 238, a lever 240 and a slit 242, where the lever 240 is moved within the slit 242. When the lever 240 is pressed down, it deploys and locks the wheel 240 in place for the PET scanner 210 to be rollable. When the lever 240 is pressed down again, it unlocks the lever 240 and retracts the wheel 240 into a stowed position within the lifting structures 214 and 216. This allows the PET scanner 210 to be stationary and stable to be used for imaging. The lever 240 can be a simple machine consisting of a rigid bar.

Referring to FIGS. 8, 9, 10, and 14, there is shown an uninterruptible power supply or uninterruptible power source (UPS) 236 which is an electrical device that provides emergency power to the PET scanner 210 when the input power source or main power fails.

Figure 15:
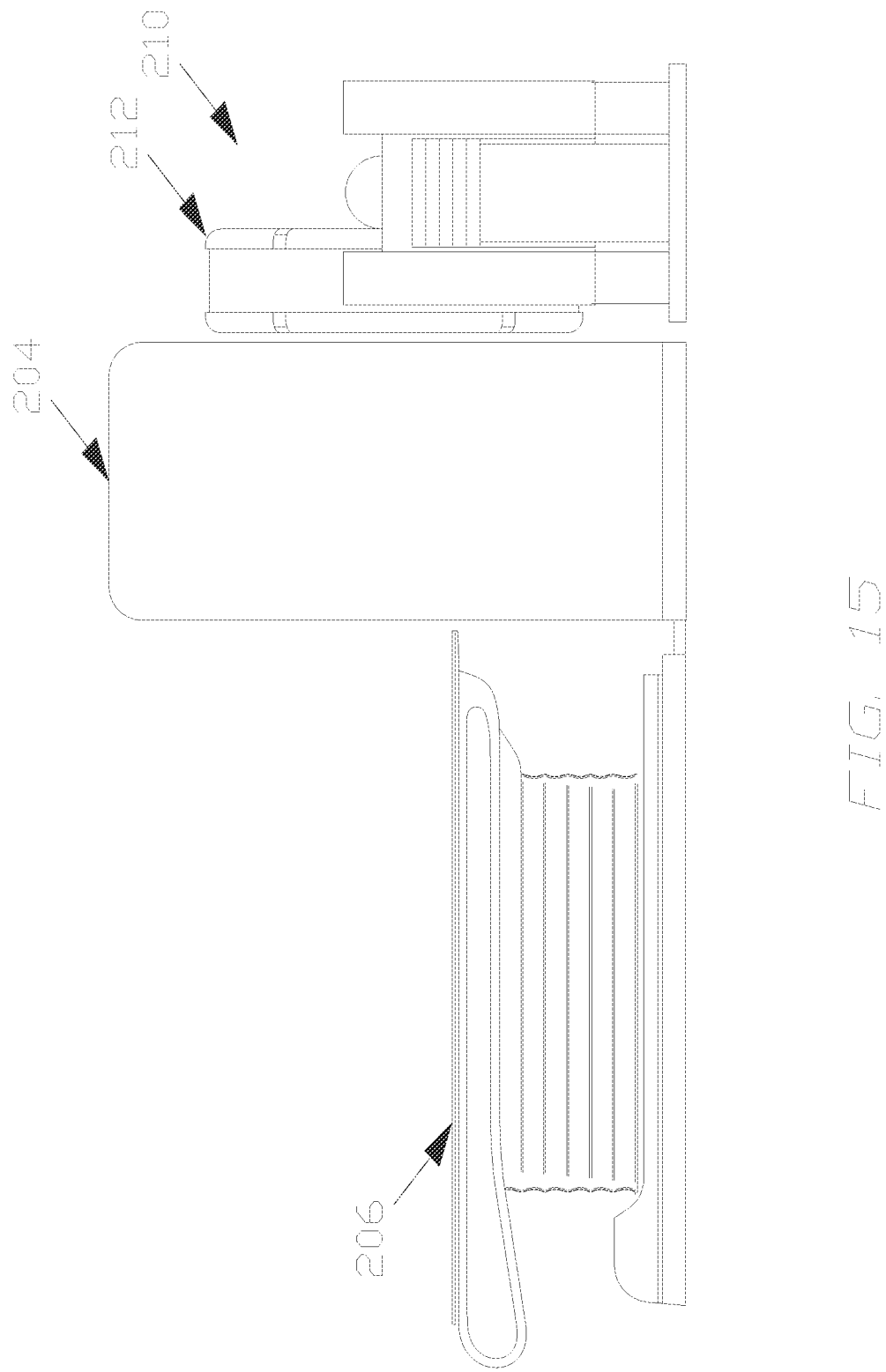
FIG. 15 is a side elevational view of the present invention portable PET scanner adapted to be used in conjunction with a prior art independent magnetic resonance imaging (MRI) scanner or computerized tomography (CT) scanner, showing the scan detector ring in a vertical orientation for imaging a patient in a horizontal configuration.

Referring to FIGS. 9, 10, and 14, there is shown portable PET scanner 210, where the scan detector ring 212 is positioned in a vertical configuration. In this configuration, the detector ring 212 is stored and secured to be moved to another location or it can be used with a gantry platform 206 by itself or adaptable and combinable with a previously installed independent computed tomography (CT) scanner or a previously installed independent magnetic resonance imaging (MRI) scanner 204 to create a hybrid PET-CT scanning system or PET-MRI scanning system for allowing a patient to be examined by both inspections one after the other as shown in FIG. 15.

Figure 16:
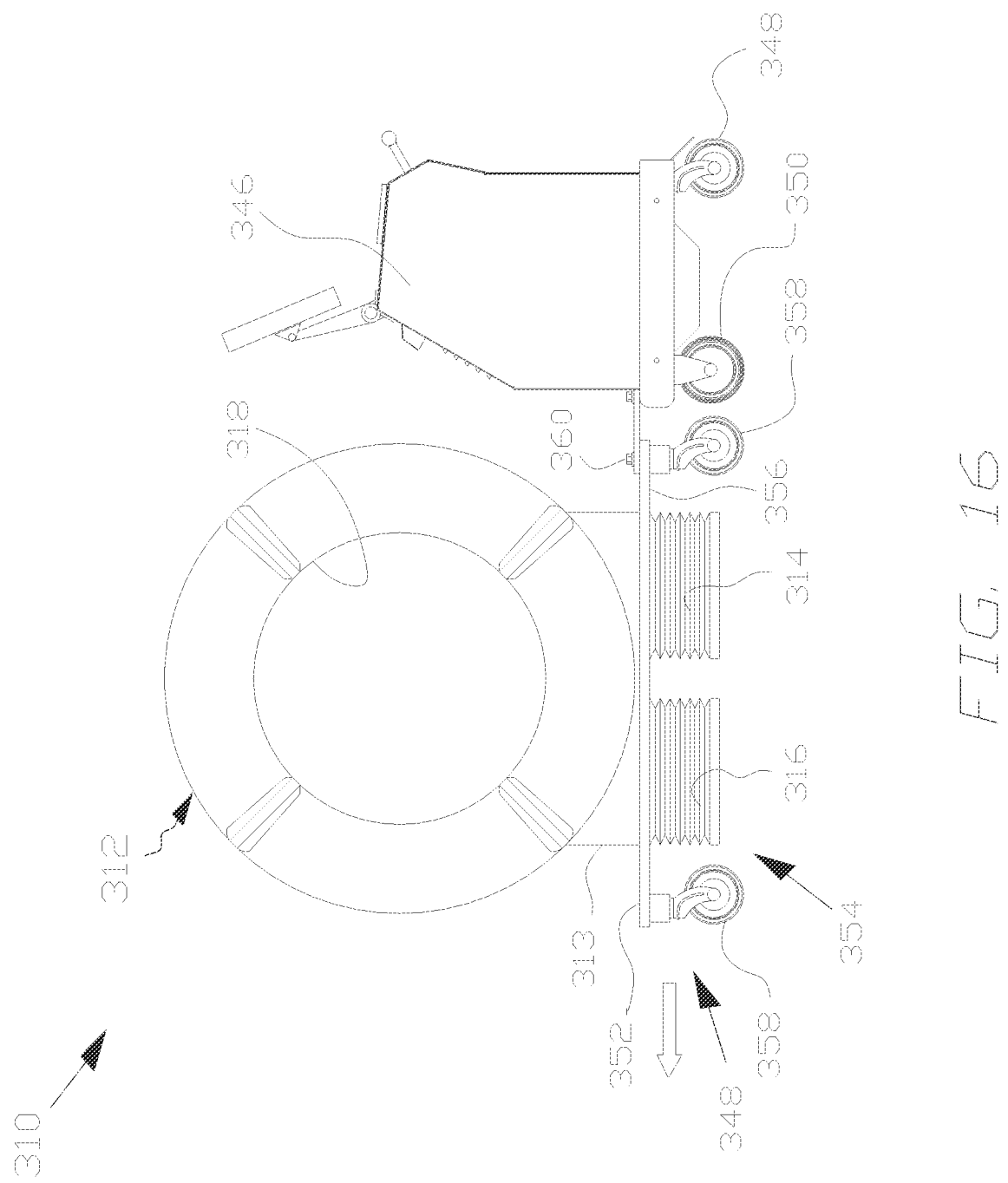
FIG. 16 is a side elevational view of an alternative embodiment of the present invention portable PET scanner with a transport apparatus for transporting the portable PET scanner.
Figure 17:
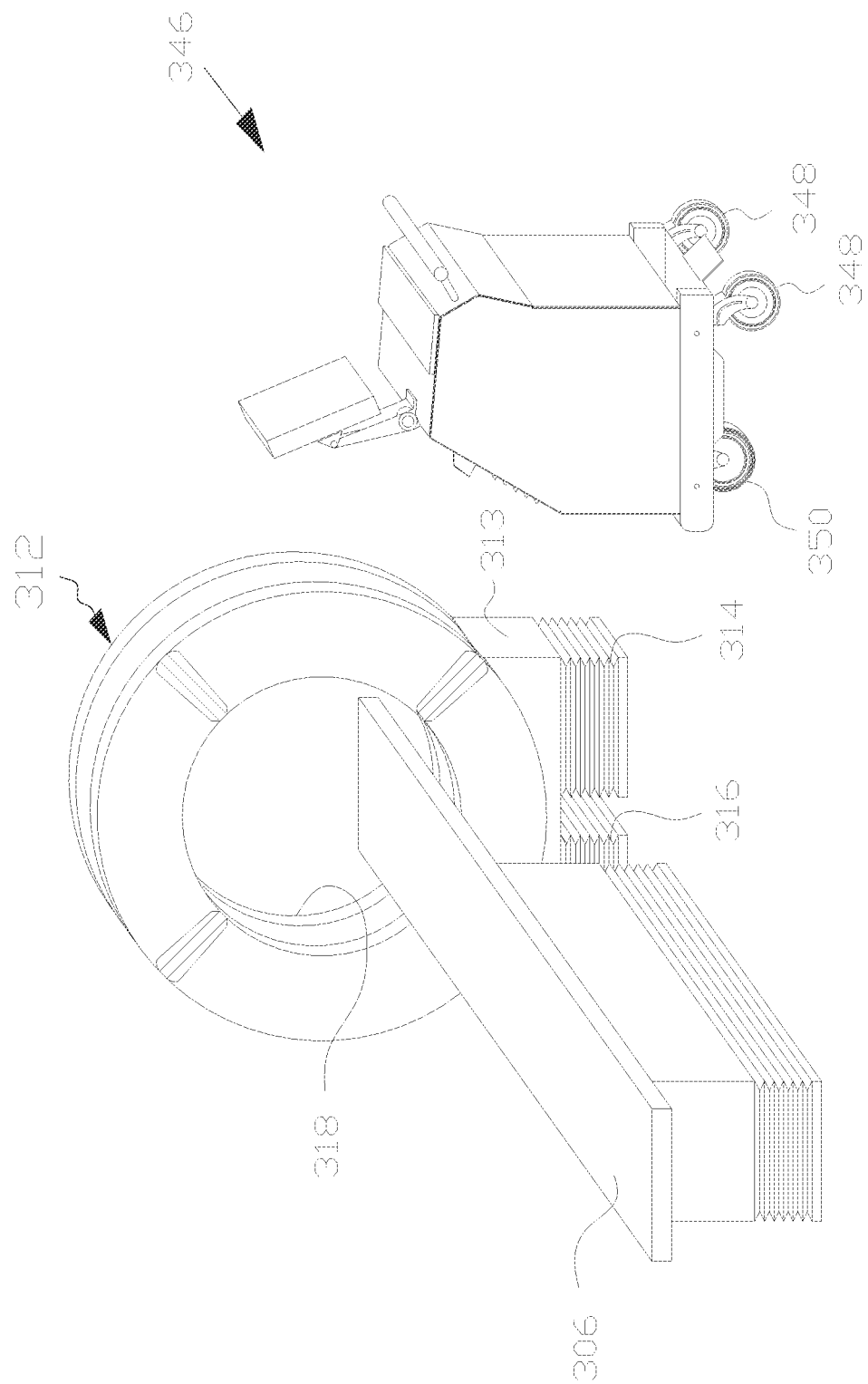
FIG. 17 is a perspective view of the alternative embodiment of the present invention portable PET scanner detached from the transport apparatus to be used with a gantry patient table for imaging a patient in the horizontal orientation.

Referring to FIGS. 16 and 17, there is shown an alternative embodiment of the present invention portable PET scanner 310 which includes a transport apparatus 354 and a computer control console 346. The PET scanner 310 includes a scan detector ring 312, a ring support structure 313 attached to a portion of the detector ring 312 for retaining the scan detector ring 312 in a vertical configuration. The scan detector ring 312 has a circular shaped aperture 318. The ring support structure 313 includes two spaced apart vertical legs 314 and 316 for retaining and positioning the scan detector ring 312 in an imaging configuration. These vertical legs 314 and 316 allows for height adjustment to the scan detector ring 312. The scan detector ring 312 has a detector depth of at least four inches and an inner diameter of at least twenty inches for fully imaging a cross section of significant organ areas of a patient. Alternatively, the scan detector ring 312 has a detector depth of at least four inches to six inches and an inner diameter of at least twenty inches to sixty inches.

The transport apparatus 354 includes an elongated transport platform 356 and four swivel wheels 358 mounted underneath the transport platform 356 for rolling movement. A yoke attachment 360 attaches the control console 346 to the transport platform 356. The control console 346 includes two swivel wheels 348 and a dual wheel motor powered caster 350, where the dual wheel motor powered caster 350 is utilized to move the transport platform 356 holding the PET scanner 310 to other imaging locations.

The PET scanner 310 is used with a gantry table 306. In response to commands received from the computer control console 346, the table 306 is moved through the aperture 318 with the patient lying down to image a patient in the scanning area of the scan detector ring 312 of the portable PET scanner 310.

The computer system typically includes a monitor and one or more input devices such as a keyboard or a mouse. Through the keyboard and associated input devices, the operator can control the operation of the PET scanner 310 and the display of the resulting images on the computer monitor. The mass of the scan detector ring 312 and its sensitive sensors and electronics is secured within the detector ring 312.

Of course the present invention is not intended to be restricted to any particular form or arrangement, or any specific embodiment, or any specific use, disclosed herein, since the same may be modified in various particulars or relations without departing from the spirit or scope of the claimed invention hereinabove shown and described of which the apparatus or method shown is intended only for illustration and disclosure of an operative embodiment and not to show all of the various forms or modifications in which this invention might be embodied or operated.

The present invention has been described in considerable detail in order to comply with the patent laws by providing full public disclosure of at least one of its forms. However, such detailed description is not intended in any way to limit the broad features or principles of the present invention, or the scope of the patent to be granted. Therefore, the invention is to be limited only by the scope of the appended claims.

What is claimed is:

1. A portable PET imaging scanner for vertically or horizontally imaging a region of interest of a patient within a scanning area, the PET imaging scanner comprising:

a stable scan detector ring having an aperture, the detector ring having a detector depth of at least four inches and a diameter of at least nine inches for fully imaging a cross section of said region of interest of said patient;

at least four vertical lifting columns spaced apart from each other and attached to a portion of said scan detector ring for providing support and to stabilize image acquisition over the minutes required for said PET imaging scanner, where said scan detector ring is located on top ends of the at least four vertical lifting columns;

at least four motorized and synchronized devices each respectively connected to said at least four vertical lifting columns for providing vertical precise repeatability imaging so that multiple cross sections are aligned within a software;

two opposite rotating slew rings attached below said scan detector ring and having rotational rolling bearings for slow-turning said scan detector ring to rotate 90 degrees into unlock and lock in the vertical or horizontal configuration for imaging said patient in both the vertical and horizontal configurations, said stable scan detector ring in the vertical or horizontal configuration has significant height to create a depth of a field to wholly image most organs of interests of said patient within a cross-section of said patient of at least 15 centimeters in height for Cardiac under stress or breast and other cancer related imagery;

at least four wheel assemblies each respectively affixed to a bottom of said each vertical lifting column such that when the at least four wheel assemblies are deployed, said portable PET imaging scanner is moved from a first location to a second location and when the at least four wheel assemblies are retracted, said PET imaging scanner is secured and stationary to be used for imaging; and an attachable control console for transporting said portable PET imaging scanner so that no ferrous components are in proximity of any imagery equipment when said scan detector ring is in the vertical or horizontal configuration, and for operator safely from radioactive emissions required for PET imaging scanner, said stable scan detector ring in either the vertical or horizontal configuration when stationary or in transport has a low center of gravity and subject to said patient movement and stress is not compromised and by providing leveling pads for patient scanning.

2. The portable PET imaging scanner in accordance with claim 1 wherein said at least four motorized and synchronized devices include electrical motors.

3. The portable PET imaging scanner in accordance with claim 1 wherein said at least four motorized and synchronized devices include hydraulic.

4. The portable PET imaging scanner in accordance with claim 1 further comprising an uninterruptible power supply (UPS) for providing emergency power to said PET scanner.

5. A portable PET imaging scanner for vertically or horizontally imaging a region of interest of a patient within a scanning area, the PET imaging scanner comprising:

a detector ring having an aperture;

four vertical lifting columns spaced apart from each other for raising or lowering said detector ring and providing support and to stabilize image acquisition over minutes required for said PET imaging scanner, where said detector ring is located on top ends of the four vertical lifting columns;

four motorized devices each respectively connected to said four vertical lifting columns for providing vertical precise repeatability imaging so that multiple cross sections are aligned within a software;

two opposite rotating slew rings attached below said detector ring and having rotational rolling bearings for slow-turning said detector ring to rotate 90 degrees into unlock and lock in the vertical or horizontal configuration for imaging said patient in both the vertical and horizontal configurations, said detector ring in the vertical or horizontal configuration has significant height to create a depth of a field to wholly image most organs of interests of said patient within a cross-section of said patient of at least 15 centimeters in height for Cardiac under stress or breast and other cancer related imagery;

four wheel assemblies each respectively affixed to a bottom of said each vertical lifting column such that when the four wheel assemblies are deployed, said portable PET imaging scanner is moved from a first location to a second location and when the four wheel assemblies are retracted, said PET imaging scanner is secured and stationary to be used for imaging; and an attachable control console for transporting said portable PET imaging scanner so that no ferrous components are in proximity of any imagery equipment when said detector ring is in the vertical or horizontal configuration, and for operator safely from radioactive emissions required for said PET imaging scanner, said detector ring in either the vertical or horizontal configuration when stationary or in transport has a low center of gravity and subject to said patient movement and stress is not compromised and by providing leveling pads for patient scanning.

6. The PET imaging scanner in accordance with claim 5 wherein said four motorized devices are synchronized.

7. The PET imaging scanner in accordance with claim 5 wherein said four motorized devices include electrical motors.

8. The PET imaging scanner in accordance with claim 5 wherein said a four motorized devices include hydraulic.

9. The PET imaging scanner in accordance with claim 5 wherein said detector ring includes a detector depth of at least four inches and a diameter of at least nine inches for fully imaging a cross section of said region of interest of said patient.

10. The PET imaging scanner in accordance with claim 5 further comprising an uninterruptible power supply (UPS) for providing emergency power to said PET scanner.

11. A portable PET imaging apparatus for horizontally imaging a region of interest of a patient within a scanning area, the apparatus comprising:

a detector ring having an aperture;

a support structure attached to a portion of said detector ring for retaining the detector ring in a vertical orientation, the support structure having two spaced apart vertical height adjustment legs for retaining and positioning said scan detector ring in an imaging configuration;

a transport platform having a yoke attachment and at least four wheels mounted underneath the transport platform for rolling movement; and a computer control console attached to said transport platform by said yoke attachment and having at least two wheels and at least one motorized wheel, where the at least one motorized wheel is utilized to move said transport platform holding said detector ring to other imaging locations, where the computer control console for controlling the scanning of said patient within said aperture of said detector ring while said patient is lying down.

12. The portable PET imaging apparatus in accordance with claim 11 wherein said detector ring includes sensitive sensors and electronics secured and enclosed within said detector ring.

13. The portable PET imaging apparatus in accordance with claim 11 wherein said detector ring includes a detector depth of at least four inches and a diameter of at least twenty inches for fully imaging a cross section of said region of interest of said patient.

* * * * *